United States Patent
Seidenberger

(10) Patent No.: US 11,857,739 B2
(45) Date of Patent: Jan. 2, 2024

(54) CATHETER FOR DIALYSIS, IN PARTICULAR FOR LONG-TERM APPLICATION

(71) Applicant: Joline GmbH & Co. KG, Hechingen (DE)

(72) Inventor: Dieter Seidenberger, Hechingen (DE)

(73) Assignee: JOLINE GMBH & CO. KG, Hechingen (DE)

( * ) Notice: Subject to any disclaimer, the term of this patent is extended or adjusted under 35 U.S.C. 154(b) by 0 days.

(21) Appl. No.: 16/638,858

(22) PCT Filed: Jul. 2, 2018

(86) PCT No.: PCT/EP2018/067755
§ 371 (c)(1),
(2) Date: Feb. 13, 2020

(87) PCT Pub. No.: WO2019/034320
PCT Pub. Date: Feb. 21, 2019

(65) Prior Publication Data
US 2021/0128879 A1    May 6, 2021

(30) Foreign Application Priority Data
Aug. 17, 2017    (DE) ............ 10 2017 118 820.7

(51) Int. Cl.
*A61M 25/02* (2006.01)
*A61M 1/36* (2006.01)
*A61M 25/00* (2006.01)

(52) U.S. Cl.
CPC .......... *A61M 25/02* (2013.01); *A61M 1/3661* (2014.02); *A61M 2025/0031* (2013.01); *A61M 2025/028* (2013.01)

(58) Field of Classification Search
CPC ............ A61M 25/02; A61M 1/3661; A61M 2025/028; A61M 2025/0031; A61M 2025/0286; A61M 2025/024
See application file for complete search history.

(56) References Cited

U.S. PATENT DOCUMENTS 4,629,243 A * 12/1986 Jensen .................. B60P 3/32
16/229
5,382,239 A * 1/1995 Orr et al. ............. A61M 25/02
604/177

(Continued)

FOREIGN PATENT DOCUMENTS

| CN | 104245032 A | 12/2014 |
| GB | 2422553 A | 8/2006 |

OTHER PUBLICATIONS

English language Abstract of CN104245032A.

*Primary Examiner* — Nilay J Shah
(74) *Attorney, Agent, or Firm* — Ware, Fressola, Maguire & Barber LLP

(57) ABSTRACT

A catheter for dialysis for long-term application features a proximal end for introducing into a blood vessel, a distal end for extracting blood and for introducing purified blood, and a fixing member surrounding a tube section for fixing the catheter on the patient. The fixing member has a receiving part and an opening part, wherein, with respect to the receiving part, the opening part can be moved from an opening position, in which the tube section is insertable into the fixing member, into a closing position, in which the tube section is fixed in the fixing member.

10 Claims, 3 Drawing Sheets

(56) References Cited

U.S. PATENT DOCUMENTS

| | | | |
|---|---|---|---|
| 5,807,311 | A | 9/1998 | Palestrant |
| 6,283,945 | B1 | 9/2001 | Bierman et al. |
| 2002/0015614 | A1* | 2/2002 | Lindsay ................ B62D 21/20 403/230 |
| 2003/0229313 | A1 | 12/2003 | Bierman et al. |
| 2004/0097903 | A1* | 5/2004 | Raulerson ........... A61M 1/3661 604/523 |
| 2004/0199122 | A1 | 10/2004 | Bierman |
| 2010/0016801 | A1 | 1/2010 | Rosenberg |
| 2013/0303986 | A1* | 11/2013 | Penalosa, Jr. ......... A61M 25/02 604/118 |
| 2014/0155801 | A1* | 6/2014 | Zinn et al. .... A61M 2025/0031 604/534 |
| 2014/0228810 | A1 | 8/2014 | Rosenberg |

\* cited by examiner

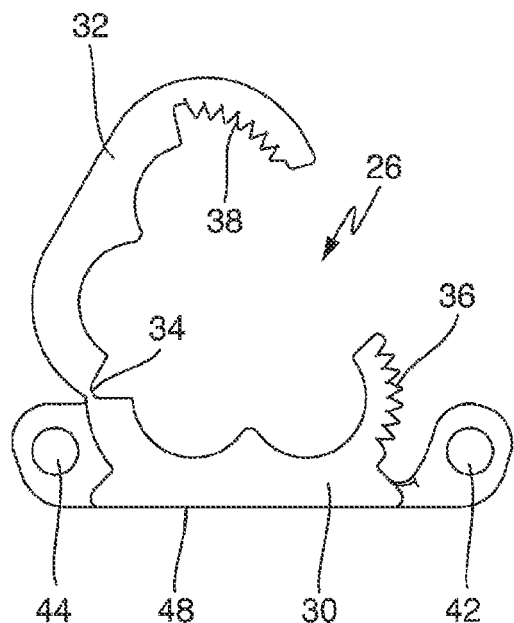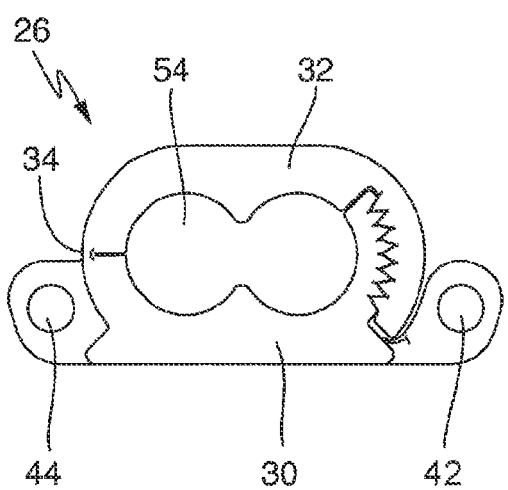
Fig. 3a  Fig. 3b
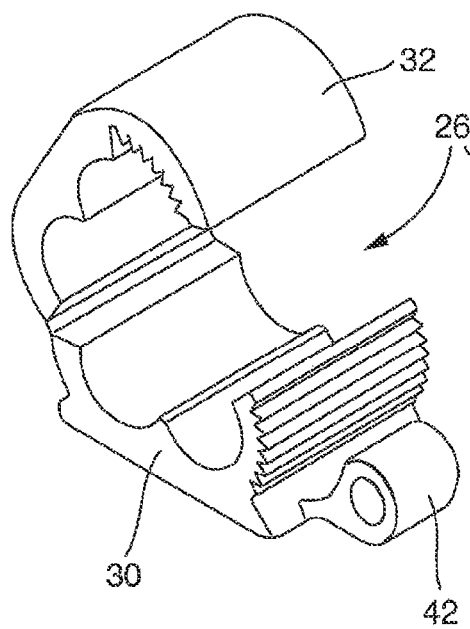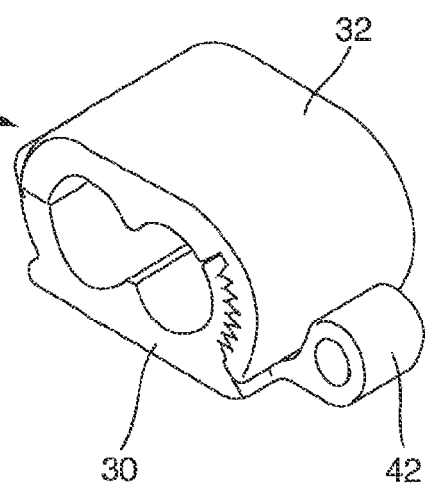
Fig. 3c  Fig. 3d

CATHETER FOR DIALYSIS, IN PARTICULAR FOR LONG-TERM APPLICATION

BACKGROUND OF THE INVENTION

1. Field of Invention

The invention relates to a catheter for dialysis, in particular for long-term application, comprising a proximal end for introducing into a blood vessel, a distal end for extracting blood and for introducing purified blood, and at least one fixing means surrounding a tube section for fixing the catheter on the patient. In the following, the term "dialysis" is understood to mean all blood purification processes, in particular hemodialysis, hemofiltration, hemodiafiltration, peritoneal dialysis, hemoperfusion and apheresis processes.

2. Description of Related Art

The catheters mentioned at the outset are known in a variety of ways from the prior art. Particularly in long-term application, these catheters remain in the patient for several days, several weeks or several months.

From DE 602 25 431 T2 and GB 2 422 553 A, such catheters are known, which have a fixing means for fixing the catheter to the patient in the form of a suture thread ring which provides thread holes by means of which the catheter can be sewn onto the patient.

From U.S. Pat. No. 6,283,945 B1 and US 2004 0 199 122 A1, catheters having features of the preamble of claim 1 are known, said catheters providing for an alternative attachment option of the catheter to the patient by means of clips on adhesive cushions. In US 2010 0 016 801 A1 and US 2014 0 228 810 A1, the attachment of the catheter by means of a hook below the skin is disclosed.

A disadvantage of the known prior art is that the centering means interfere with the movement of the catheter. In addition, in long-term application it can be advantageous for hygienic reasons to replace or remove a fixing means that is fixed in the body close to the point of entry of the catheter.

SUMMARY OF THE INVENTION

The object of the invention is to propose a catheter of the type mentioned, which is simple to replace.

This object is achieved by a catheter having the features of claim 1. The catheter consequently provides that the fixing means has a receiving part and an opening part, wherein, with respect to the receiving part, the opening part can be moved from an opening position, in which the tube section is insertable into the fixing means, into a closing position, in which the tube section is fixed in the fixing means.

It is thereby achieved that the catheter or the tube section can be inserted into the fixation means after the catheter has been placed, assuming its final position. The fixing means can be attached to the respective tube section and finally sewn onto the patient. When the catheter or a tube section is replaced, the opening part can advantageously be shifted from the closing position back into the opening position, so that the tube section can be removed from the fixing means.

The receiving part has at least one eyelet for fixing the receiving part on the patient. By means of the eyelet, the receiving part can be, in particular, sewn on the patient. Preferably, two or more eyelets are provided on the receiving part.

Furthermore, the opening part has an eyelet, which is located in the closing position in axial extension next to the eyelet of the receiving part. The adjacent eyelets can then together be penetrated by, for example, a thread, wherein this thread also serves for sewing the fixing means on the patient. This prevents the opening part from being opened without removing the thread.

The receiving part can in particular be connected to the opening part by means of a film hinge. As a result, the opening part is arranged securely on the receiving part, and can nevertheless be moved from the opening position into the closing position and back.

The receiving part preferably provides a latching section. The opening part preferably provides a counter-latching section which interacts with the latching section, the latching section being locked in the closing position with the counter-latching section. The provision of such latching has the advantage that no further components for securing the opening part in the closing position on the receiving part are required.

The latching is preferably designed such that it can be released with a tool, and in particular with a surgical instrument such as a thread-pulling knife. The latching is preferably such that it cannot be released without a suitable tool. This ensures that the patient cannot move the opening part out of the closing position.

It is also advantageous if the receiving part and the opening part have an inner contour which is at least largely complementary to the outer contour of the tube section. This ensures that the tube section is securely arranged in the fixing means. The design can be such that an axial displacement of the tube section in the fixing means is excluded. The design can also be such that two tube sections joined together and arranged one behind the other in the axial direction are securely connected to one another by means of the fixing means in the closing position.

The receiving part can also have a flat support section on its underside facing the patient. This ensures that the receiving part can rest comfortably on the patient.

It is furthermore advantageous, if the catheter has two tube sections which run parallel to one another, each forming at least one lumen, wherein a first fixing means is provided which receives these two tube sections. For example, the blood extracted from the patient can be supplied in a tube section; in the other tube section the cleaned blood to be supplied to the patient can be supplied. A tube section forming these two lumens is preferably provided proximal to the first fixing means, it being possible for a second fixing means to be provided which receives this one tube section. The two lumens, which run in separate tubes in the distal region, can consequently be transferred into a common tube section by means of an appropriate coupling means. This common tube section can then also be attached to the patient with an appropriate fixing means.

Further details and advantageous designs of the invention can be found in the following description, on the basis of which exemplary embodiments of the invention are explained and described in more detail.

BRIEF DESCRIPTION OF THE DRAWING

In the drawings:

FIGS. 3a to d show the other fixing means shown in FIG. 1.

DETAILED DESCRIPTION OF THE BEST MODE OF THE INVENTION

Figure 1:
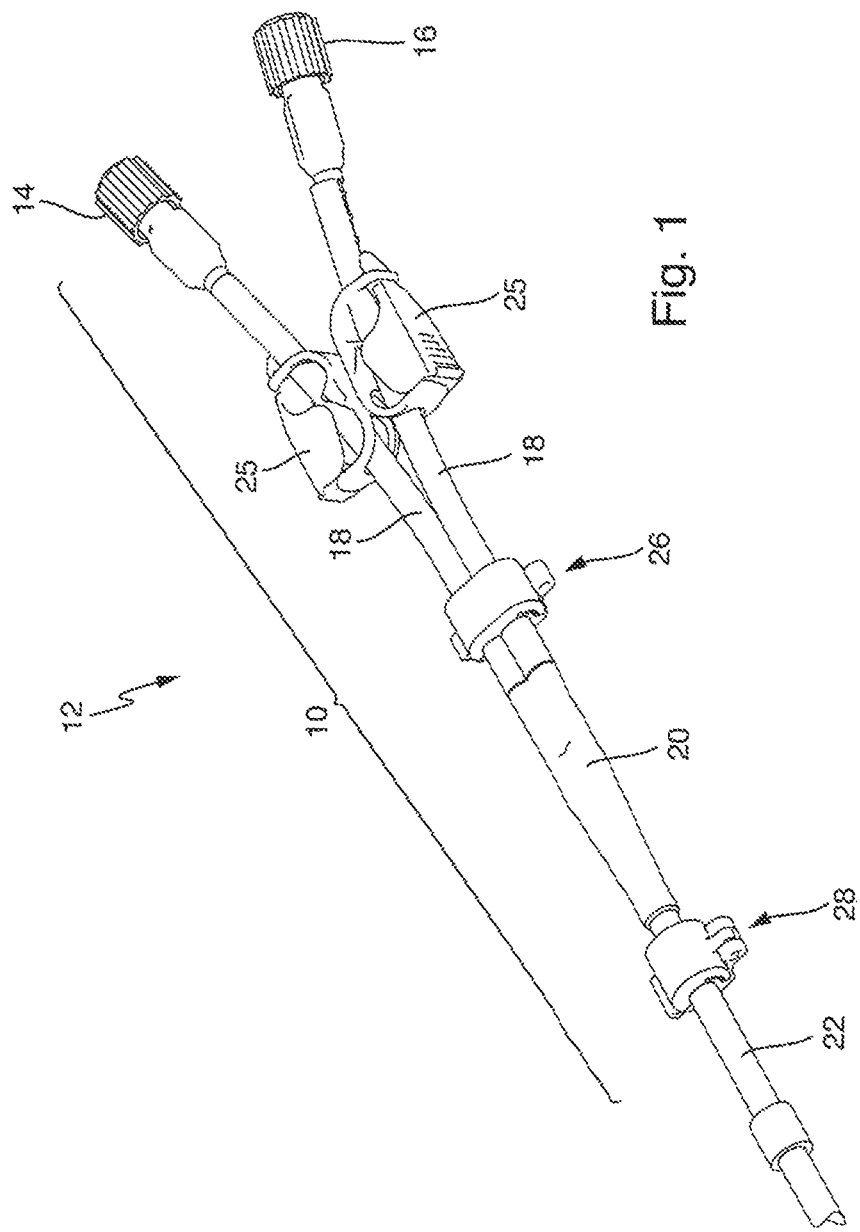
FIG. 1 shows the distal end of a catheter according to the invention having two fixing means.

FIG. 1 shows the distal end 10 of a catheter 12 for dialysis. An outlet 14 is provided at the distal end 10, by means of which the extracted blood can be fed to a dialyzer.

An inlet 16 is also provided, by means of which purified blood can be supplied to the patient. A tube section 18 is provided on the outlet 14 and on the inlet 16, the two tube sections 18 opening into a coupling part 20. In the coupling part 20, the lumens of the two tube sections 18 are coupled into a two-lumen tube section 22. On the single-lumen tube sections 18, clamping means 25 are additionally arranged with which the tube sections 18 can be closed.

When using the catheter 12, the proximal end (not shown in the Figures) is inserted into a blood vessel, in particular into the right auricle. Especially in long-term application, the catheter 12 remains in or on the patient for several weeks or months. In order to securely fix the catheter 12 to the patient, the catheter 12 provides two fixing means 26 and 28, which are shown as an individual part in FIGS. 2 and 3. The insertion and placement of the catheter 12 is executed without the two fixing means 26 and 28. After the catheter 12 has reached its final position, the fixing means 26, 28 can be clipped onto the respective tube section 18, 22 of the catheter 12. The fixing means 26 then surrounds the two single-lumen tube sections 18. The fixing means 28 surrounds the double-lumen tube section 22.

As is clear from FIGS. 2 and 3, the fixing means 26 and 28 each have a receiving part 30 and an opening part 32, wherein the opening part 32 can be moved from an opening position, which is shown in FIGS. 2a, 2c and 3a, 3c, to a closing position, which is shown in FIG. 2b, 2d and FIG. 3b, 3d. The opening part 32 is arranged on the receiving part 30 by means of a film hinge 34. The fixing means 26, 28 are preferably made of plastic and are formed in one piece.

The receiving parts 30 each have a latching section 36 which, in the closing position, interacts with a counter-latching section 38 provided on the opening part 32. In the closing position, the latching section 36, or the teeth thereof, is in the counter-latching section 38, or between the teeth thereof.

As is clear from FIG. 2, a total of three eyelets 40, 42 and 44 are formed on the receiving part 30. The two eyelets 40 and 42 are arranged parallel to one another and have a common longitudinal axis 46.

On the underside, the receiving part 30 has a flat support section 48 which extends into the underside of the eyelets 40, 42 and 44. The support section 48 is used for contact with the patient.

Figure 2A:
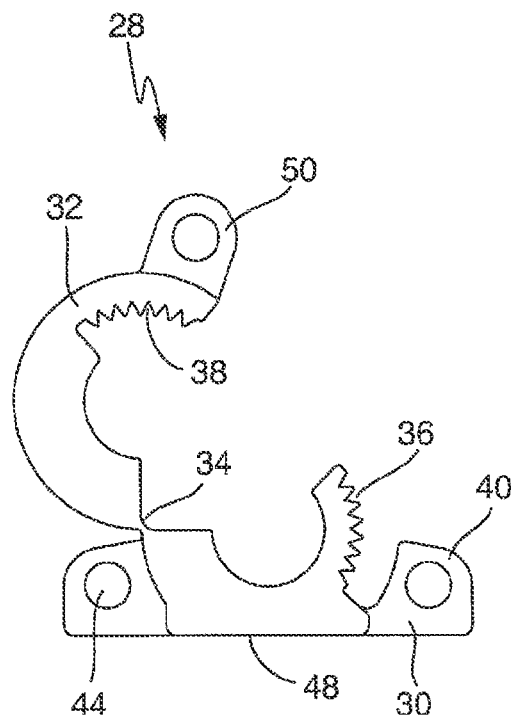
FIGS. 2a to d show one of the two fixing means shown in FIG. 1.
Figure 2B:
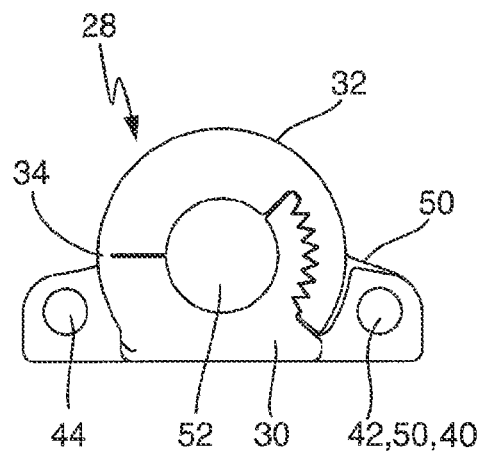
Figure 2C:
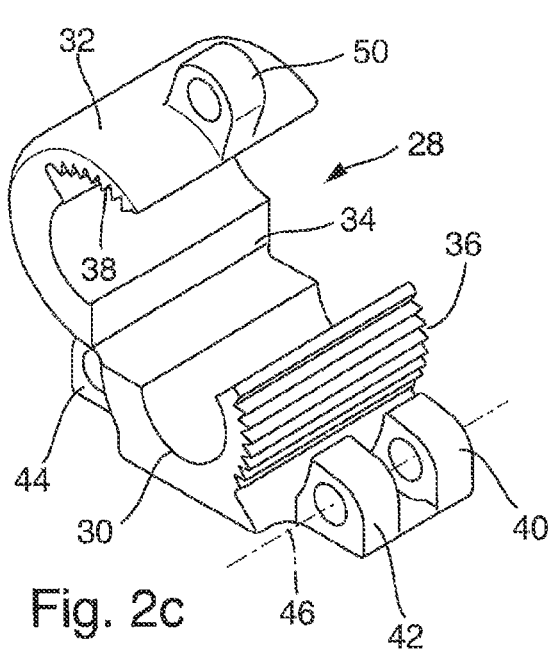
Figure 2D:
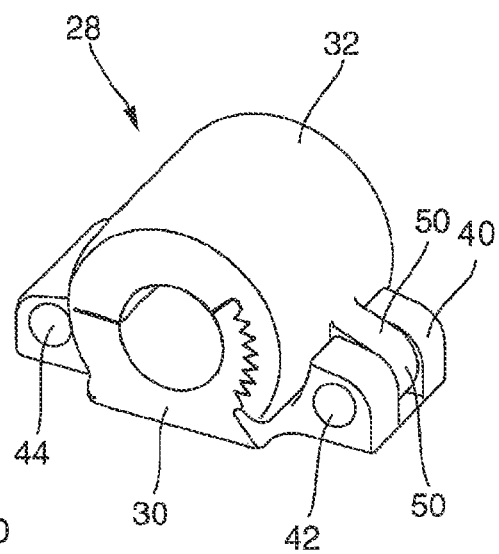

As is also clear from FIG. 2, an eyelet 50 is likewise provided on the opening part 32 and, in the closing position, as is clear from FIGS. 2b and 2d, comes to rest between the two eyelets 40, 42 adjacent to the receiving part. Consequently, in the closing position, the eyelet 50 of the opening part 32 is between the two eyelets 42, 40 adjacent to the receiving part.

The receiving part 30 and the opening part 32 have a circular inner contour 52, which corresponds to the outer contour of the tube section 22, but has a somewhat smaller diameter, such that the tube section 22 is arranged in the closing position under slight prestress in the fixing means and is secured in the axial direction.

The fixing means 28 is sewn onto the patient by means of suitable threads onto the patient. A thread is passed through the eyelets 42, 50 and 40 and is attached to the patient. Another thread is passed through the eyelet 44 and is also sewn to the patient. In the long-term application of the catheter 12, the fixing means 28, which is close to the point at which the catheter 12 is inserted into the patient, can be removed after 4-6 weeks for hygienic reasons.

The fixing means 26 shown in FIG. 3 essentially corresponds to the fixing means 28. Each component is provided with corresponding reference numerals. In contrast to the fixing means 28, the fixing means 26 receives the two tube sections 18 extending parallel to one another. For this reason, the inner contour 54 of the fixing means 26 is designed to be complementary to the outer contour of the tube sections 18. In contrast to the fixing means 28, the fixing means 26 can also be opened when it is sewn on the patient.

Both fixing means 26 and 28 have the advantage that they can only be placed onto the respective tube sections 18, 22 after the catheter 12 has been inserted and placed in the patient.

The invention claimed is:

1. A catheter (12) for dialysis, having a proximal end for introducing into a blood vessel, a distal end (10) for extracting blood and for introducing purified blood, and at least one fixing means (26, 28) surrounding a tube section (18, 22) for fixing the catheter (12) on a patient,
    the at least one fixing means (26, 28) having a receiving part (30) and an opening part (32);
    with respect to the receiving part (34), the opening part (32) being configured to move from an opening position, in which the tube section (18, 22) is insertable into the at least one fixing means (26, 28), into a closing position, in which the tube section (18, 22) is fixed in the at least one fixing means (26, 28);
    the opening part (32) being arranged on the receiving part (30) by means of a film hinge (34), the receiving part (30) having at least one eyelet (40, 42, 44) and the opening part (32) has at least one corresponding eyelet (50);
    the at least one corresponding eyelet (50) of the opening part (32) being located in the closing position in axial extension along a common longitudinal axis (46) next to the at least one eyelet (40, 42, 44) of the receiving part (30), such that adjacent eyelets can be penetrated together by a thread guided along the common longitudinal axis (46) for fixing the at least one fixing means (26, 28) on the patient;
    the receiving part (30) having an underside facing the patient with a flat support section (48);
    the common longitudinal axis (46) extending parallel to the flat support section (48) and the film hinge (34), characterized in that
    the at least one fixing means (26, 28) comprises a first fixing means (26) and a second fixing means (28);
    the catheter (12) has two tube sections (18) which run parallel to one another and each form at least one lumen;
    the first fixing means (26) is provided which receives the two tube sections (18); and
    the second fixing means (28) is provided proximal to the first fixing means(26) and receives a tube section (22) forming the at least two lumens.

2. The catheter (12) according to claim 1, characterized in that the receiving part (30) has a latching section (36), and the opening part (32) has a counter-latching section (38), wherein the latching section (36) is locked in the closing position with the counter-latching section (38).

3. The catheter (12) according to claim 2, characterized in that the counter-latching section (38) is configured to release from the latching section (36) by means of a tool.

4. The catheter (12) according to claim 1, characterized in that the receiving part (30) and the opening part (32) have an inner contour (52, 54) which is at least largely complementary to an outer contour of the tube section (18, 22).

5. The catheter (12) according to claim 1, characterized in that the fixing means (26, 28) comprises a film hinge (34) configured to connect the receiving part (30) to the opening part (32).

6. A catheter (12) for dialysis, comprising:
- a proximal end for introducing into a blood vessel;
- a distal end (10) for extracting blood and for introducing purified blood,
- two tube sections (18) configured to run parallel to one another and each form at least one lumen;
- a tube section (22) configured to form at least two lumens;
- a coupling part (20) configured to couple together the two tube sections (18) and the tube section (22);
- a first fixing means (26) having a receiving part (30) and a opening part (32) configured to receive and surround the two tube sections (18);
- a second fixing means (28) provided proximal to the first fixing means (26), having a corresponding receiving part (30) and a corresponding opening part (32) configured to receive and surround the tube section (22);
- each opening part (32) configured to receive either the two tube sections (18) or the tube section (22), and move from a respective opening position to a respective closing position for fixing the two tube sections (18) and the tube section (22) into the first fixing means (26) and the second fixing means (28);
- the first fixing means (26) and the second fixing means (28) each having a respective film hinge (34) configured to attach each opening part (32) to each receiving part (30);
- each receiving part (30) having at least one eyelet (40, 42);
- the opening part (32) of the second fixing means having a corresponding eyelet (50);
- the corresponding eyelet (50) of the opening part (32) being located in the respective closing position next to the at least one eyelet (40, 42) of the respective receiving part (30) so as to form adjacent eyelets (40, 42; 50) when the receiving part (30) and the opening part (32) are in the respective closing position; and
- the adjacent eyelets (40, 42; 50) configured to receive and be penetrated by a thread guided along the common longitudinal axis (46) for sewing the first fixing means (26) and the second fixing means (28) and the catheter onto the patient.

7. The catheter (12) according to claim 6, wherein
- each receiving part (30) has a respective latching section (36);
- each opening part (32) has a respective counter-latching section (38); and
- the respective latching section (36) is locked in the closing position with the respective counter-latching section (38).

8. The catheter (12) according to claim 7, wherein the respective counter-latching section (38) is configured to release from the respective latching section (36), including by means of a tool.

9. The catheter (12) according to claim 8, wherein each receiving part (30) and each opening part (32) have a respective inner contour (52, 54) which is substantially complementary to an outer contour of the tube section (18, 22).

10. The catheter (12) according to claim 6, wherein
- each receiving part (30) has a respective eyelet (44) in addition to the at least one eyelet (40, 42); and
- the respective eyelet (44) is configured to be penetrated by a respective thread guided for fixing the first fixing means (26) and the second fixing means (28) on the patient.

* * * * *